United States Patent
Amemiya et al.

(10) Patent No.: US 6,786,867 B2
(45) Date of Patent: Sep. 7, 2004

(54) ULTRASONIC DIAGNOSTIC APPARATUS

(75) Inventors: Shinichi Amemiya, Tokyo (JP); Osamu Furuta, Tokyo (JP); Yoshinori Sakamoto, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 37 days.

(21) Appl. No.: 10/128,024

(22) Filed: Apr. 23, 2002

(65) Prior Publication Data

US 2003/0018254 A1 Jan. 23, 2003

(30) Foreign Application Priority Data

Apr. 25, 2001 (JP) ........................................ 2001-126974

(51) Int. Cl.⁷ ............................................... A61B 8/00
(52) U.S. Cl. ....................................................... 600/437
(58) Field of Search .............................. 600/437, 447; 128/920, 923; 73/620

(56) References Cited

U.S. PATENT DOCUMENTS

| | | | |
|---|---|---|---|
| D298,854 S | * 12/1988 | Kame et al. | D24/1.1 |
| D334,062 S | * 3/1993 | Davis et al. | D24/160 |
| 5,703,932 A | * 12/1997 | Oda | 379/58 |
| 5,722,412 A | 3/1998 | Pflugrath et al. | 600/459 |
| 5,999,167 A | 12/1999 | Marsh et al. | |
| 6,142,940 A | 11/2000 | Lathbury et al. | |
| 6,288,457 B1 | 9/2001 | Kako et al. | |
| 6,361,497 B1 | * 3/2002 | Lathbury et al. | 600/437 |
| 6,491,630 B1 | 12/2002 | Saccardo et al. | 600/437 |
| 6,497,661 B1 | 12/2002 | Brock-Fisher | 600/437 |
| D469,539 S | * 1/2003 | Felix et al. | D24/187 |
| 6,540,685 B1 | * 4/2003 | Rhoads et al. | 600/459 |
| 6,569,101 B2 | * 5/2003 | Quistgaard et al. | 600/459 |

* cited by examiner

*Primary Examiner*—Francis J. Jaworski
(74) *Attorney, Agent, or Firm*—Carl B. Horton, Esq.; Armstrong Teasdale LLP

(57) ABSTRACT

In order to allow operation of key switches without awkwardly bending the elbow or wrist, and arranging key switches aesthetically in the appearance design while preventing confusion in operation and eliminating dead space within the area occupied by the key switches, key switches 1-1–1-6 are arranged horizontally in a row slantingly with respect to the horizontal and vertical directions of an operation panel 101.

17 Claims, 7 Drawing Sheets

ULTRASONIC DIAGNOSTIC APPARATUS

CROSS REFERENCE TO RELATED APPLICATIONS

This application claims the benefit of Japanese Application No. 2001-126974 filed Apr. 25, 2001.

BACKGROUND OF THE INVENTION

The present invention relates to an ultrasonic diagnostic apparatus, and more particularly to an ultrasonic diagnostic apparatus in which key switches can be operated without awkwardly bending the elbow or wrist, and such an ultrasonic diagnostic apparatus in which the key switches can be arranged aesthetically in the appearance design while preventing confusion in operation and eliminating dead space within the area occupied by the key switches.

FIG. 1 is a plan view showing an example of an operation panel in a conventional ultrasonic diagnostic apparatus.

The operation panel 51 is provided with an LCD display 21, vertical key switches 52 and horizontal key switches 53 for increasing/decreasing setting values relating to imaging and display of an ultrasonic image, an operation pad 22 and a keyboard 23.

The vertical key switches 52 are associated with adjustment in which an increase/decrease of a setting value gives the impression of an increase/decrease in the vertical direction. For example, adjustment of the baseline shift in an ultrasonic Doppler technique gives the impression of vertical moving of a zero frequency axis, and therefore the adjustment is performed by the vertical key switch 52.

The horizontal key switches 53 are associated with adjustment in which an increase/decrease of a setting value gives the impression of an increase/decrease in the horizontal direction. For example, adjustment of the cutoff frequency gives the impression of horizontal shifting of the filter characteristic in a frequency characteristic diagram having a frequency axis as a horizontal axis, and therefore the adjustment is performed by the horizontal key switch 53.

In the conventional ultrasonic diagnostic apparatus, since the vertical and horizontal key switches 52 and 53 are disposed together on the operation panel 51, the following problems arise:

(1) When an operation is performed using the right index finger and middle finger, for example, the vertical key switches 52 have to be operated with the elbow opened outward and the wrist bent inward. Similarly, the horizontal switches 53 have to be operated with the elbow shut inward and the wrist bent outward. In other words, the elbow and wrist must be awkwardly bent and the operator suffers from difficulty.

(2) When the vertical and horizontal key switches 52 and 53 are disposed together, since the operational directions of the vertical and horizontal key switches 52 and 53 are different, confusion in operation may result.

(3) When the vertical and horizontal key switches 52 and 53 are disposed together, dead space is apt to occur within the area occupied by the key switches on the operation panel 51 and in the space occupied by switch bodies in the interior of the operation panel 51.

(4) When the vertical and horizontal key switches 52 and 53 are disposed together, the aesthetics of the appearance design is degraded.

SUMMARY OF THE INVENTION

It is therefore a first object of the present invention to provide an ultrasonic diagnostic apparatus in which key switches can be operated without awkwardly bending the elbow or wrist.

Moreover, it is a second object of the present invention to provide an ultrasonic diagnostic apparatus in which the key switches can be arranged aesthetically in the appearance design while preventing confusion in operation and eliminating dead space within the area occupied by the key switches.

In accordance with a first aspect, the present invention is an ultrasonic diagnostic apparatus having an operation panel provided with a plurality of key switches for increasing/decreasing setting values relating to imaging and display of an ultrasonic image, wherein one or more key switches are disposed slantingly with respect to the horizontal and vertical directions of the operation panel.

In the ultrasonic diagnostic apparatus of the first aspect, since the key switches are disposed slantingly with respect to the horizontal and vertical directions of the operation panel, the key switches can be operated using the index and middle fingers without awkwardly bending the elbow or wrist.

In accordance with a second aspect, the present invention is the ultrasonic diagnostic apparatus of the aforementioned configuration, wherein the slanting key switches include two key switches for baseline shifting and for cutoff frequency setting.

In the ultrasonic diagnostic apparatus of the second aspect, adjustment of the baseline shift in which an increase/decrease of the setting value gives the impression of an increase/decrease in the vertical direction and adjustment of the cutoff frequency in which an increase/decrease of the setting value gives the impression of an increase/decrease in the horizontal direction can be performed by the same operation with the same position of the elbow and wrist, and therefore confusion of the operator can be prevented.

In accordance with a third aspect, the present invention is the ultrasonic diagnostic apparatus of the aforementioned configuration, wherein a plurality of the slanting key switches are arranged in a horizontal row or in a vertical row.

In the ultrasonic diagnostic apparatus of the third aspect, since a plurality of the slanting key switches are arranged in a horizontal row or in a vertical row, dead space within the area occupied by the key switches is eliminated and the appearance design can be aestheticized as compared with the case in which the vertical and horizontal key switches are disposed together.

In accordance with a fourth aspect, the present invention is the ultrasonic diagnostic apparatus of the aforementioned configuration, wherein the slanting key switch includes a key top that is operated by a human operator's finger, and a switch body for performing a switching action by operating the key top.

In the ultrasonic diagnostic apparatus of the fourth aspect, since the key top and the switch body are separated, the degree of freedom in design can be improved.

In accordance with a fifth aspect, the present invention is the ultrasonic diagnostic apparatus of the aforementioned configuration, wherein the switch body is a seesaw switch that performs a switching action by an operation of seesawing the position of the key top.

In the ultrasonic diagnostic apparatus of the fifth aspect, since one key top and the seesaw switch are employed, the configuration is suitable for single-option adjustment.

In accordance with a sixth aspect, the present invention is the ultrasonic diagnostic apparatus of the aforementioned configuration, wherein the switch body comprises a pair of push switches that perform a switching action by an operation of seesawing the position of the key top.

In the ultrasonic diagnostic apparatus of the sixth aspect, since one key top and the push switches are employed, the configuration is suitable for single-option adjustment.

In accordance with a seventh aspect, the present invention is the ultrasonic diagnostic apparatus of the aforementioned configuration, wherein the key top comprises a pair of key tops arranged in a slanting direction, and the switch body comprises a pair of push switches that perform a switching action by an operation of pushing one of the pair of key tops.

In the ultrasonic diagnostic apparatus of the seventh aspect, since two key tops and two push switches are employed, a special operation of pushing both of the key tops is allowed.

In accordance with an eighth aspect, the present invention is the ultrasonic diagnostic apparatus of the aforementioned configuration, wherein the switch body is a rotation encoder by which an output value varies by an operation of sliding the key top.

In the ultrasonic diagnostic apparatus of the eighth aspect, since one key top and the rotation encoder are employed, the configuration is suitable for a case in which a setting value is continuously adjusted.

In accordance with a ninth aspect, the present invention is the ultrasonic diagnostic apparatus of the aforementioned configuration, wherein the switch body is a slide switch that performs a switching action by an operation of sliding the key top.

In the ultrasonic diagnostic apparatus of the ninth aspect, since one key top and the slide switch are employed, the configuration is suitable for single-option adjustment.

In accordance with a tenth aspect, the present invention is the ultrasonic diagnostic apparatus of the aforementioned configuration, wherein the key top is slanted at an angle of 20°–60° counterclockwise with respect to a horizontal direction of the operation panel.

In the ultrasonic diagnostic apparatus of the tenth aspect, an operation can be performed using the index and middle fingers with the elbow and wrist in a natural attitude.

In accordance with an eleventh aspect, the present invention is the ultrasonic diagnostic apparatus of the aforementioned configuration, wherein the key top has a curved shape with a sagging center.

In the ultrasonic diagnostic apparatus of the eleventh aspect, since a key top having a curved shape with a sagging center is employed, the configuration is suitable for an operation with a finger placed on the end of the key top.

In accordance with a twelfth aspect, the present invention is the ultrasonic diagnostic apparatus of the aforementioned configuration, wherein the key top has a curved shape with a bulging center.

In the ultrasonic diagnostic apparatus of the twelfth aspect, since a key top having a curved shape with a bulging center is employed, the configuration is suitable for an operation with a finger placed on the center of the key top.

In accordance with a thirteenth aspect, the present invention is the ultrasonic diagnostic apparatus of the aforementioned configuration, wherein the key top has a flat shape.

In the ultrasonic diagnostic apparatus of the thirteenth aspect, since a key top having a flat shape is employed, an operation with a finger placed on the end of the key top or on the center of the key top is allowed.

In accordance with a fourteenth aspect, the present invention is the ultrasonic diagnostic apparatus of the aforementioned configuration, wherein a protrusion is provided in the center of the key top.

In the ultrasonic diagnostic apparatus of the fourteenth aspect, since a protrusion is provided in the center of the key top, an operation with one finger is allowed with the finger placed on the protrusion.

In accordance with a fifteenth aspect, the present invention is the ultrasonic diagnostic apparatus of the aforementioned configuration, wherein the key top is provided with marks representing an oblique direction.

In the ultrasonic diagnostic apparatus of the fifteenth aspect, the same key top may be used either in adjustment in which an increase/decrease of a setting value gives the impression of an increase/decrease in the vertical direction or in adjustment in which an increase/decrease of a setting value gives the impression of an increase/decrease in the horizontal direction.

In accordance with a sixteenth aspect, the present invention is the ultrasonic diagnostic apparatus of the aforementioned configuration, wherein the key top is provided with marks representing the vertical direction.

In the ultrasonic diagnostic apparatus of the sixteenth aspect, confirmation can be made that a setting value to be adjusted by a key switch corresponds to adjustment that gives the impression of an increase/decrease in the vertical direction by looking at the marks.

In accordance with a seventeenth aspect, the present invention is the ultrasonic diagnostic apparatus of the aforementioned configuration, wherein the key top is provided with marks representing the horizontal direction.

In the ultrasonic diagnostic apparatus of the seventeenth aspect, confirmation can be made by looking at the marks that a setting value to be adjusted by a key switch corresponds to adjustment that gives the impression of an increase/decrease in the horizontal direction.

According to the ultrasonic diagnostic apparatus of the present invention, key switches can be operated without awkwardly bending the elbow or wrist. Moreover, adjustment in which an increase/decrease of a setting value gives the impression of an increase/decrease in the vertical direction and adjustment in which an increase/decrease of a setting value gives the impression of an increase/decrease in the horizontal direction can be performed by the same operation, and confusion in operation can be prevented. Furthermore, key switches can be arranged to eliminate dead space within the area occupied by the key switches and offer an aesthetic appearance design.

Further objects and advantages of the present invention will be apparent from the following description of the preferred embodiments of the invention as illustrated in the accompanying drawings.

DETAILED DESCRIPTION OF THE INVENTION

Embodiments of the present invention will now be described with reference to accompanying drawings. It should be noted that the present invention is not limited to these embodiments.

First Embodiment

Figure 2:
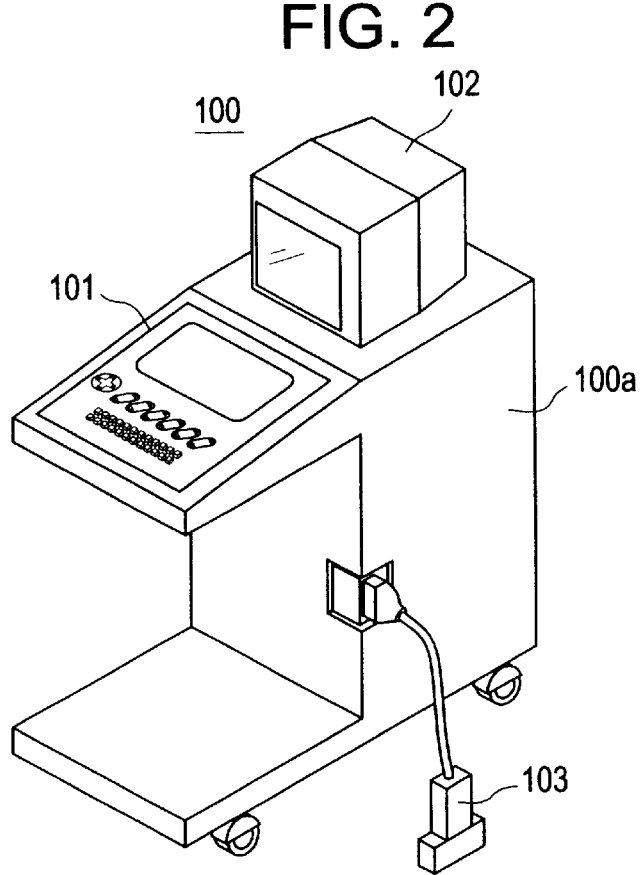
FIG. 2 is a perspective view showing an ultrasonic diagnostic apparatus in accordance with a first embodiment.

FIG. 2 is a perspective view showing an ultrasonic diagnostic apparatus in accordance with a first embodiment of the present invention. The ultrasonic diagnostic apparatus 100 comprises an ultrasonic diagnostic apparatus body 100a including an operation panel 101 and a CRT display device 102, and an ultrasonic probe 103 for transmitting/receiving ultrasound.

Figure 3:
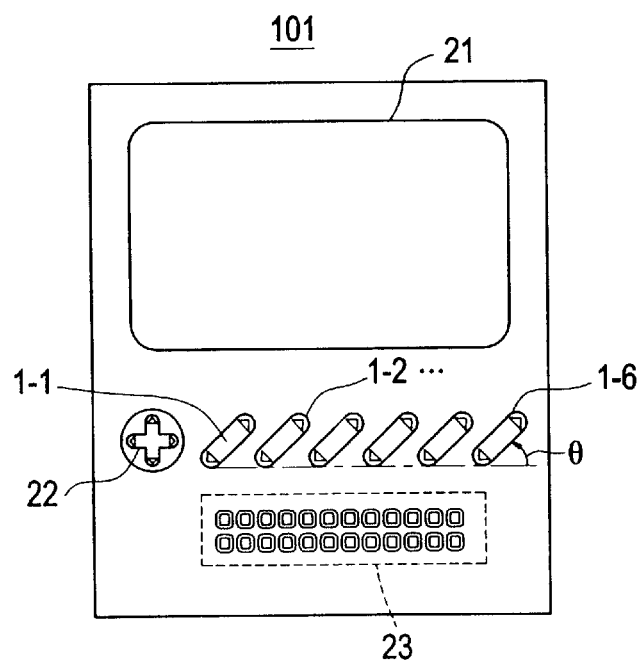
FIG. 3 is a plan view showing an operation panel in accordance with the first embodiment.

FIG. 3 is a plan view showing the operation panel 101.

The operation panel 101 is provided with an LCD display 21, key switches 1-1, 1-2, . . . , 1-6 arranged in a row slantingly with respect to the horizontal and vertical directions of the operation panel 101, an operation pad 22 for moving a cursor up-and-down and right-and-left, and a keyboard 23 for inputting numeral values and commands.

The slanting angle θ of the key switch 1 is 20°–60° counterclockwise with respect to a horizontal direction of the operation panel 101, and is 45°, for example.

The key switches 1-1, 1-2 and 1-5 are assigned to adjustment of the baseline shift etc. in which an increase/decrease of a setting value gives the impression of an increase/decrease in the vertical direction.

The key switches 1-3, 1-4 and 1-6 are assigned to adjustment of the cutoff frequency etc. in which an increase/decrease of a setting value gives the impression of an increase/decrease in the horizontal direction.

Figure 4:
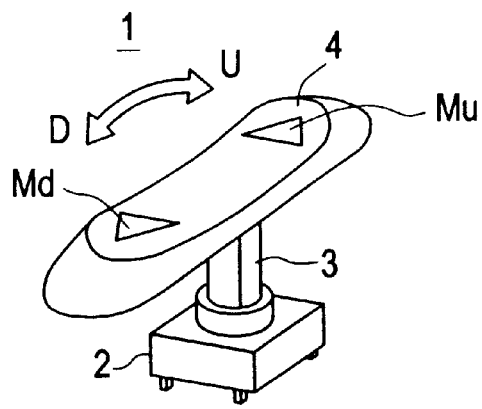
FIG. 4 is a perspective view showing a key switch in accordance with the first embodiment.

FIG. 4 is a perspective view showing one of the key switches 1 (=1-1–1-6).

The key switch 1 is comprised of a key top 4 with a slightly sagging center, and a seesaw switch 2 that performs a switching action by an operation of seesawing the position of the key top 4 causing a stick 3 to incline.

The key top 4 is provided with marks Mu and Md at its both ends, which marks point outward along the longitudinal direction of the key top 4.

When no external force is applied, the seesaw switch 2 makes the stick 3 stand upright by an elastic force.

Figure 5:
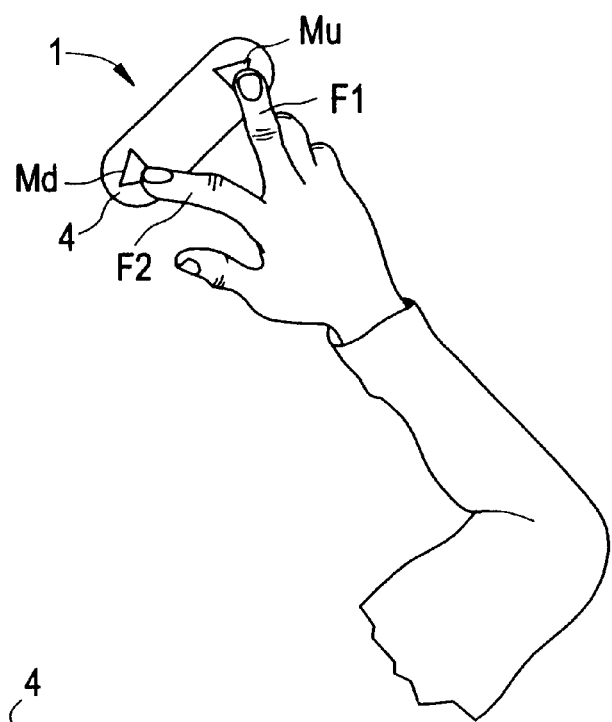
FIG. 5 is an explanatory view showing operation of the key switch in accordance with the first embodiment.

FIG. 5 is an explanatory view showing operation of the key switch 1.

Figure 6:
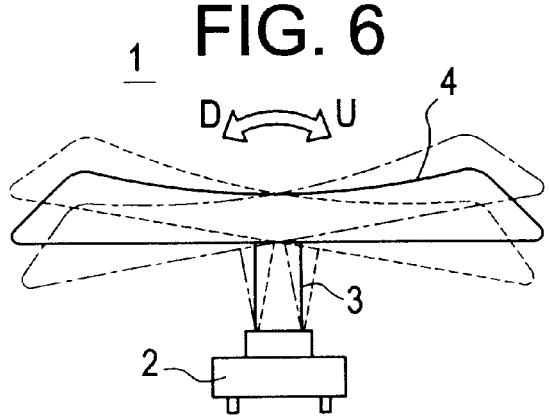
FIG. 6 is a side view showing rocking of a key switch in accordance with the first embodiment.

A human operator places the right middle finger F1 on the oblique upward mark Mu on the key top 4, and the index finger F2 on the oblique downward mark Md, for example. If a setting value is to be increased, the operator pushes down the middle finger F1 to incline the stick 3 as indicated by a broken line in FIG. 6. If a setting value is to be decreased, the operator pushes down the index finger F2 to incline the stick 3 as indicated by a dot-dash line in FIG. 6.

According to the ultrasonic diagnostic apparatus 100 of the first embodiment, the following effects can be obtained:

(1) The key switches 1-1–1-6 can be operated without awkwardly bending the elbow or wrist. Therefore, the operator is free from difficulty and the operation is easy.

(2) Since adjustment that gives the impression of adjustment in the vertical direction (e.g., adjustment of the baseline shift) and adjustment that gives the impression of adjustment in the horizontal direction (e.g., adjustment of the cutoff frequency) can be performed by the same operation, confusion in operation is prevented.

(3) Since the slanting key switches 1-1, 1-2, . . . , 1-6 are arranged horizontally in a row, dead space within the area occupied by the key switches on the operation panel 101 and in the space occupied by switch bodies in the interior of the operation panel 101 is eliminated as compared with the case in which the vertical and horizontal key switches are disposed together.

(4) Since the slanting key switches 1-1, 1-2, . . . , 1-6 are arranged horizontally in a row, the appearance design can be aestheticized as compared with the case in which the vertical and horizontal key switches are disposed together.

(5) Since one key top 4 and the seesaw switch 2 are employed, the configuration is suitable for single-option adjustment.

Second Embodiment

Figure 7:
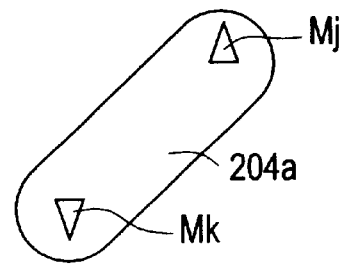
FIG. 7 is a plan view showing a key switch in accordance with a second embodiment.

As shown in FIG. 7, a key top 204a provided with an upward mark Mj and a downward mark Mk may be used, in place of the oblique upward mark Mu and the oblique downward mark Md in the first embodiment.

Figure 8:
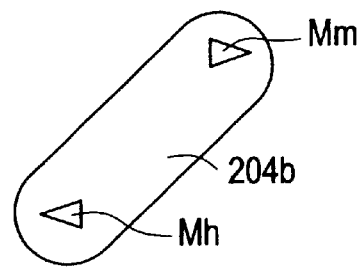
FIG. 8 is another plan view showing a key switch in accordance with the second embodiment.

Moreover, as shown in FIG. 8, a key top 204b provided with a rightward mark Mm and a leftward mark Mh may be used, in place of the oblique upward mark Mu and the oblique downward mark Md in the first embodiment.

Figure 9:
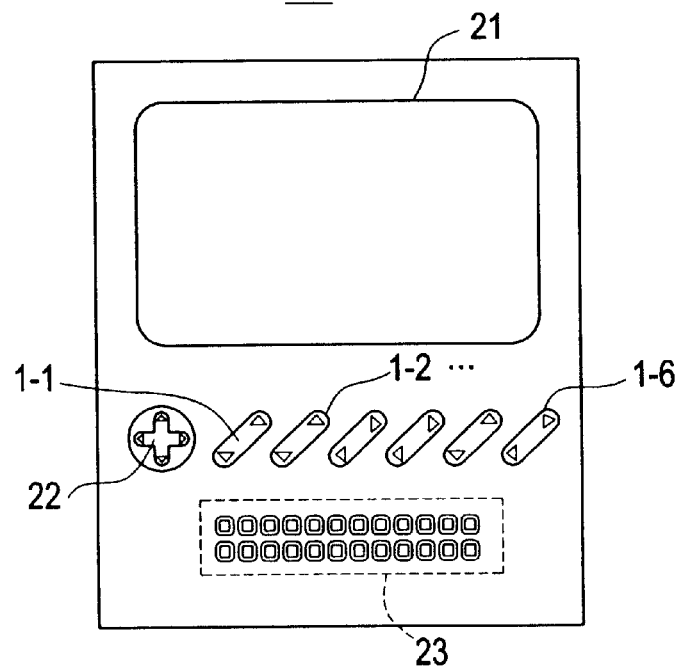
FIG. 9 is a plan view showing an operation panel in accordance with the second embodiment.

In this case, the operation panel 101 is such one as shown in FIG. 9.

According to the ultrasonic diagnostic apparatus of the second embodiment, in addition to the effects (1)–(5) in the first embodiment, the following effect can be obtained: confirmation can be made that setting values that give the impression of adjustment in the vertical direction are to be adjusted using the key switches 1-1, 1-2 and 1-5 from the upward mark Mj and the downward mark Mk; and confirmation can be made that setting values that give the impression of adjustment in the horizontal direction are to be adjusted using the key switches 1-3, 1-4 and 1-6 from the rightward mark Mm and the leftward mark Mh.

Third Embodiment

Figure 10:
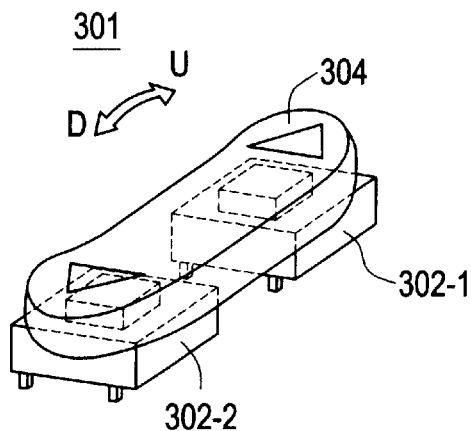
FIG. 10 is a perspective view showing a key switch in accordance with a third embodiment.

FIG. 10 is a perspective view showing a key switch in an ultrasonic diagnostic apparatus in accordance with a third embodiment.

The key switch 301 comprises a key top 304 of a flat shape, and a pair of push switches 302-1 and 302-2 that perform a switching action by an operation of seesawing the position of the key top 303.

According to the ultrasonic diagnostic apparatus of the third embodiment, in addition to the effects (1)–(4) in the first embodiment, the configuration is suitable for single-option adjustment because one key top 304 and the push switches 302-1 and 302-2 are employed.

Fourth Embodiment

Figure 11:
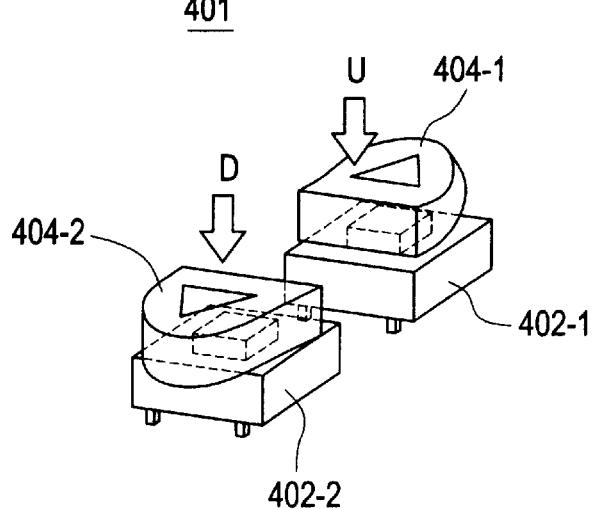
FIG. 11 is a perspective view showing a key switch in accordance with a fourth embodiment.

FIG. 11 is a perspective view showing a key switch in an ultrasonic diagnostic apparatus in accordance with a fourth embodiment.

The key switch 401 comprises a pair of key tops 404-1 and 404-2, and a pair of push switches 402-1 and 402-2 that perform a switching action by an operation of pushing one of the pair of key tops 404-1 and 404-2.

According to the ultrasonic diagnostic apparatus of the fourth embodiment, in addition to the effects (1)–(4) in the first embodiment, a special operation of pushing both of the key tops 404-1 and 404-2 is allowed.

Fifth Embodiment

Figure 12:
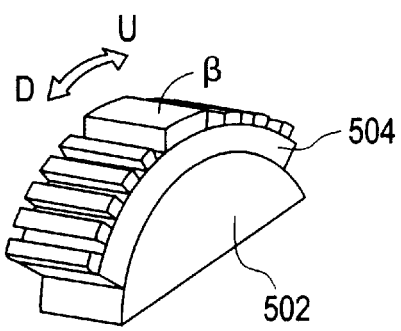
FIG. 12 is a perspective view showing a key switch in accordance with a fifth embodiment.

FIG. 12 is a perspective view showing a key switch in an ultrasonic diagnostic apparatus in accordance with a fifth embodiment.

The key switch 501 comprises a key top 504 of a curved shape with a bulging center and having a protrusion β in the center, and a rotation encoder 502 by which an output value varies by an operation of sliding the key top 504.

According to the ultrasonic diagnostic apparatus of the fifth embodiment, in addition to the effects (1)–(4) in the first embodiment, the configuration is suitable for a case in which a setting value is continuously adjusted, because the rotation encoder 502 by which an operation amount can be detected with high resolution is employed. Moreover, an operation can be performed with one finger by placing the finger on the central protrusion β of the key top 504.

Sixth Embodiment

Figure 13A:
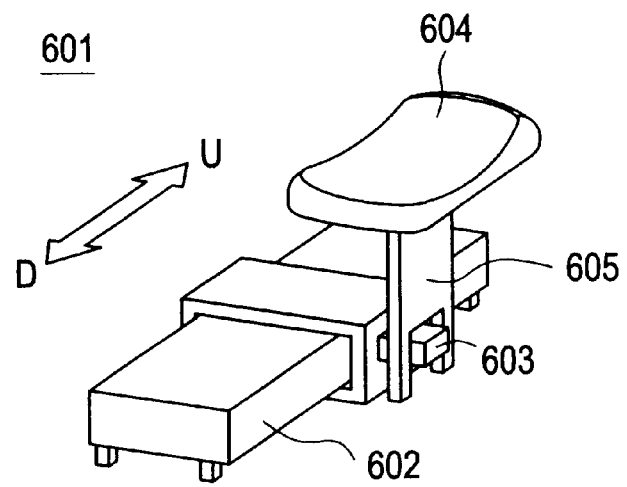
FIG. 13 is a perspective view showing a key switch in accordance with a sixth embodiment.
Figure 13B:
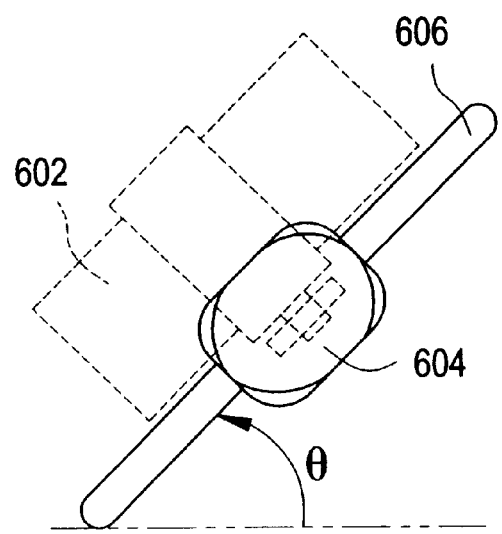

FIG. 13(*a*) is a perspective view showing a key switch in an ultrasonic diagnostic apparatus in accordance with a sixth embodiment. FIG. 13(*b*) is a top view showing a key switch in an ultrasonic diagnostic apparatus in accordance with a sixth embodiment.

The key switch 601 comprises a key top 604, and a slide switch 602 that performs a switching action by an operation of sliding the key top 604.

A lock plate 605 in the key top 604 is engaged with a slide lever 603 in the slide switch 602.

According to the ultrasonic diagnostic apparatus of the sixth embodiment, in addition to the effects (1)–(4) in the first embodiment, the configuration is suitable for single-option adjustment because one key top 604 and the slide switch 602 are employed.

Seventh Embodiment

Figure 14:
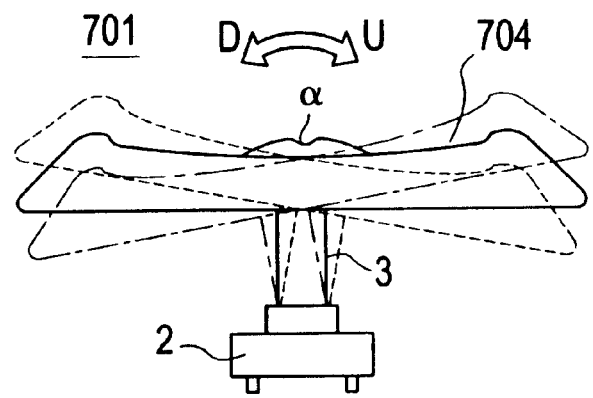
FIG. 14 is a side view showing a key switch in accordance with a seventh embodiment.

FIG. 14 is a side view showing a key switch in an ultrasonic diagnostic apparatus in accordance with a seventh embodiment.

The key switch 701 comprises a key top 704 of a flat shape and having a protrusion α in the center, and a seesaw switch 2 for performing a switching action by an operation of rocking the key top 704.

Figure 15:
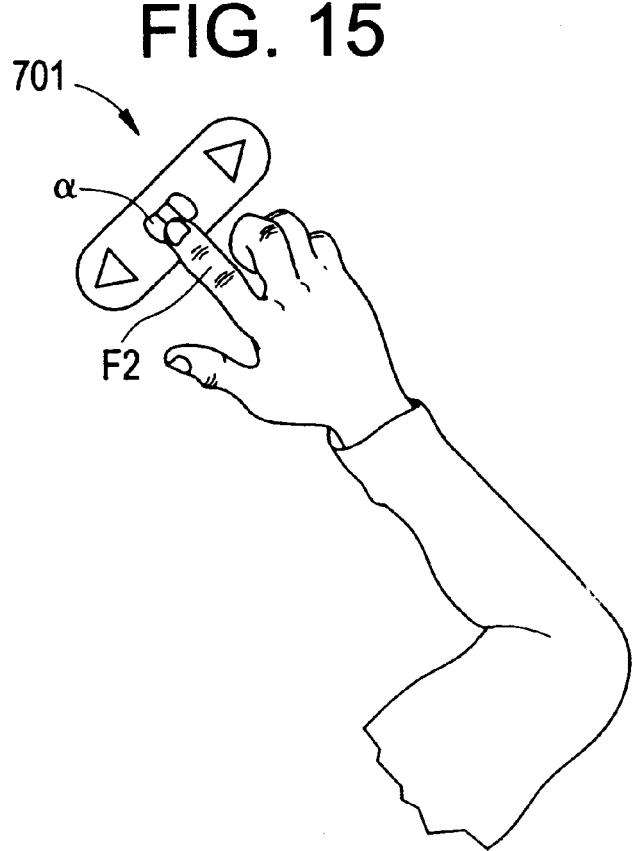
FIG. 15 is an explanatory view showing operation of the key switch in accordance with the seventh embodiment.

As shown in FIG. 15, an operation can be performed with one finger by placing an index finger F2, for example, on the protrusion α and rocking the key top 704.

According to the ultrasonic diagnostic apparatus of the seventh embodiment, in addition to the effects (1)–(5) in the first embodiment, an operation can be performed with one finger by placing the finger on the protrusion α in the center of the key top 704.

Eighth Embodiment

Figure 1:
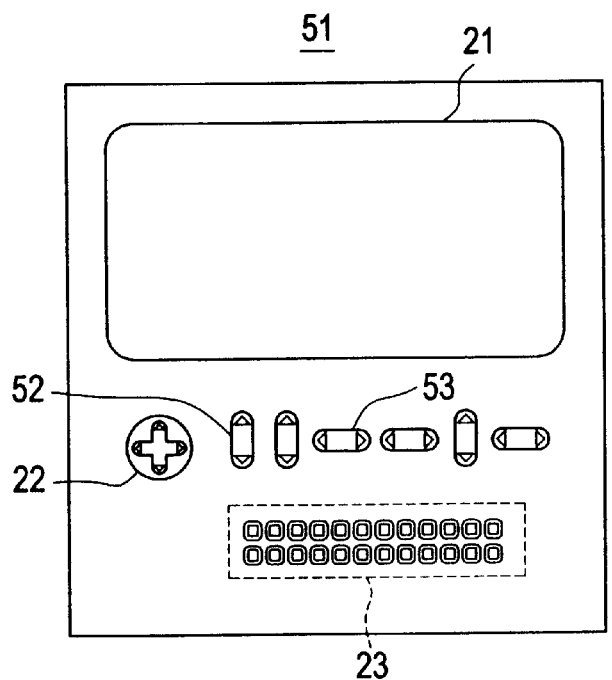
FIG. 1 is a plan view showing an example of an operation panel in a conventional ultrasonic diagnostic apparatus.
Figure 16:
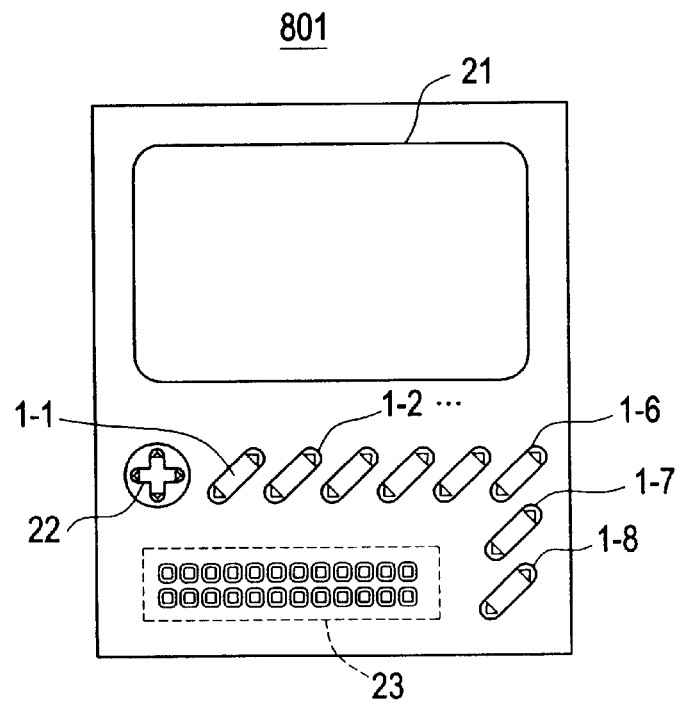
FIG. 16 is a plan view showing an operation panel in accordance with an eighth embodiment.

FIG. 16 is a plan view showing an operation panel 801 in an ultrasonic diagnostic apparatus in accordance with an eighth embodiment.

In the operation panel 801, key switches 1-1–1-6 are arranged horizontally in a row, and key switches 1-6–1-8 are arranged vertically in a row.

According to the ultrasonic diagnostic apparatus of the eighth aspect, the same effects as (1)–(5) in the first embodiment can be obtained.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic diagnostic apparatus having an operation panel provided with a plurality of key switches, each said key switch being adapted for increasing and decreasing setting values relating to imaging and display of an ultrasonic image, said key switches having an operational axis disposed at a slant with respect to the horizontal and vertical directions of the face of the operation panel.

2. The ultrasonic diagnostic apparatus as defined by claim 1, wherein the slanting key switches include two key switches for baseline shifting and for cutoff frequency setting.

3. The ultrasonic diagnostic apparatus as defined by claim 1, wherein a plurality of the slanting key switches are arranged in at least one of a horizontal row and a vertical row.

4. The ultrasonic diagnostic apparatus as defined by claim 1, wherein the slanting key switch comprises a key top that is operated by a human operator's finger, and a switch body for performing a switching action by operating said key top.

5. The ultrasonic diagnostic apparatus as defined by claim 4, wherein said switch body is a seesaw switch that performs a switching action by an operation of seesawing the position of said key top.

6. The ultrasonic diagnostic apparatus as defined by claim 4, wherein said switch body comprises a pair of push switches that perform a switching action by an operation of seesawing the position of said key top.

7. The ultrasonic diagnostic apparatus as defined by claim 4, wherein said key top comprises a pair of key tops arranged in a slanting direction, and said switch body comprises a pair of push switches that perform a switching action by an operation of pushing one of said pair of key tops.

8. The ultrasonic diagnostic apparatus as defined by claim 4, wherein said switch body is a rotation encoder by which an output value varies by an operation of sliding said key top.

9. The ultrasonic diagnostic apparatus as defined by claim 4, wherein said switch body is a slide switch that performs a switching action by an operation of sliding said key top.

10. The ultrasonic diagnostic apparatus as defined by claim 4, wherein the key top is slanted at an angle of between 20° and 60° counterclockwise with respect to a horizontal direction of the operation panel.

11. The ultrasonic diagnostic apparatus as defined by claim 4, wherein said key top has a curved shape with a sagging center.

12. The ultrasonic diagnostic apparatus as defined by claim 4, wherein said key top has a curved shape with a bulging center.

13. The ultrasonic diagnostic apparatus as defined by claims 4, wherein said key top has a flat shape.

14. The ultrasonic diagnostic apparatus as defined by claim 11, wherein a protrusion is provided in the center of said key top.

15. The ultrasonic diagnostic apparatus as defined by claim 4, wherein said key top is provided with marks representing the oblique direction.

16. The ultrasonic diagnostic apparatus as defined by claim 4, wherein said key top is provided with marks representing the vertical direction.

17. The ultrasonic diagnostic apparatus as defined by claim 4, wherein said key top is provided with marks representing the horizontal direction.

* * * * *